US008397550B2

(12) United States Patent
Huber et al.

(10) Patent No.: US 8,397,550 B2
(45) Date of Patent: Mar. 19, 2013

(54) METHOD FOR DETERMINING THE IGNITABILITY OF A FUEL

(75) Inventors: Karl Huber, Eichstatt (DE); Johann Hauber, Neuburg (DE)

(73) Assignee: Rofa Laboratory & Process Analyzers, Kritzendorf (AT)

( * ) Notice: Subject to any disclaimer, the term of this patent is extended or adjusted under 35 U.S.C. 154(b) by 146 days.

(21) Appl. No.: 12/988,950

(22) PCT Filed: Apr. 22, 2009

(86) PCT No.: PCT/EP2009/054845
§ 371 (c)(1),
(2), (4) Date: Jan. 8, 2011

(87) PCT Pub. No.: WO2009/130255
PCT Pub. Date: Oct. 29, 2009

(65) Prior Publication Data
US 2011/0192216 A1     Aug. 11, 2011

(30) Foreign Application Priority Data
Apr. 22, 2008     (DE) .......................... 10 2008 001 307

(51) Int. Cl.
*G01N 33/22* (2006.01)

(52) U.S. Cl. .................. 73/35.02; 73/114.38; 73/114.53

(58) Field of Classification Search .................. 73/35.02, 73/114.38, 114.53
See application file for complete search history.

(56) References Cited

U.S. PATENT DOCUMENTS

| | | | | |
|---|---|---|---|---|
| 4,633,707 A * | 1/1987 | Haddox | ........................... | 73/47 |
| 5,325,837 A * | 7/1994 | Laufer | ........................... | 123/506 |
| 6,125,690 A * | 10/2000 | Kitching | ..................... | 73/35.02 |
| 6,609,413 B1 | 8/2003 | De Craecker | | |
| 7,421,884 B2 * | 9/2008 | Aoyama | ..................... | 73/35.02 |
| 7,621,174 B2 * | 11/2009 | Takaku | ..................... | 73/114.53 |
| 7,946,157 B2 | 5/2011 | Habets | | |
| 8,042,517 B2 * | 10/2011 | Nakajima | ................ | 123/406.41 |
| 2006/0217872 A1 * | 9/2006 | Moriya et al. | ................ | 701/114 |
| 2007/0079647 A1 * | 4/2007 | Aoyama | ..................... | 73/35.02 |
| 2007/0163542 A1 | 7/2007 | Kettl et al. | | |
| 2007/0204674 A1 | 9/2007 | Takaku | | |
| 2011/0000579 A1 * | 1/2011 | Allinson et al. | ................ | 141/9 |

OTHER PUBLICATIONS

German Patent Office Search Report, Apr. 14, 2009.
PCT Search Report, Sep. 28, 2009.
International Preliminary Report on Patentability, Nov. 23, 2010.

* cited by examiner

*Primary Examiner* — Freddie Kirkland, III
(74) *Attorney, Agent, or Firm* — Dority & Manning, P.A.

(57) ABSTRACT

A method for determining the ignitability of a fuel, in particular a self-igniting fuel, based on the ignition delay of the fuel during the combustion in a test engine. According to the invention, the ignition delay is determined from the combustion curve and/or the heat curve.

26 Claims, 4 Drawing Sheets

METHOD FOR DETERMINING THE IGNITABILITY OF A FUEL

FIELD OF THE INVENTION

The invention refers to a method for determining the ignitability of a fuel, especially of a self-igniting fuel, based on the fuel's ignition delay during combustion inside a test engine.

BACKGROUND

Standard DIN EN 590 stipulates the minimum requirements for the characteristic values and properties of diesel fuels. Table 1 shows an overview of the important characteristic values for fuel.

TABLE 1

| Product Name Standard Last updated on Holborn item no. | Diesel (sulphur-free) Diesel fuel EN 590 (February 2000) February 2002 | | | | [logo] Holborn Europa Raffinerie GmbH Specifications |
|---|---|---|---|---|---|
| | | Diesel | | DIN EN 590 | |
| Parameter | Unit | min | max | min | max | Testing procedure |
| Appearance | | clear, free of sediments and soluble acid fractions (TAN) | | | | Visual |
| Color | | | 2 | | | ISO 2049 |
| Density at 15° C. | kg/m$^3$ | 820 | 845 | 820 | 845 | EN ISO 12185 |
| Flash point n.P.M. | ° C. | 59 | | >55 | | EN 22719 |
| Sulphur content | mg/kg | | 10 | | 10 | DIN EN ISO 14596 and DIN 51400 T11 |
| Viscosity at 40° C. | mm$^2$/s | 2.0 | 4.5 | 2.0 | 4.5 | EN ISO 3104 |
| Boiling pattern until 250° C. | Vol % | | <65 | | <65 | EN ISO 3405 |
| Boiling pattern until 350° C. | Vol % | 85 | | 85 | | EN ISO 3405 |
| 95 vol. % point | ° C. | | 360 | | 360 | EN ISO 3405 |
| Cetane number CFR test engine | | 51.0 | | 51.0 | | EN ISO 5165 |
| Cetane number BASF test engine | | 52.2 | | 52.2 | | DIN 51773 |
| Cetane index | | 46 | | 46 | | EN ISO 4264 |
| Total dirt accumulation | mg/kg | | 24 | | 24 | EN 12662 |
| Neutralization number | mgKOH/g | | 0.2 | | 0.2 | DIN 51 558 |
| Con. carbon. V. 10% dest. residue | Weight % | | 0.3 | | 0.3 | EN ISO 10370 |
| Copper corrosion (3 h 50° C.) | Corr. degree | | 1 | | 1 | EN ISO 2160 |
| Electrical conductivity | pS/m | 50 | | | | DIN 51 412-2 |
| Oxidation stability | g/m$^3$ | | 25 | | 25 | EN ISO 12205 |
| Cloud point | | | | | | |
| Summer product | ° C. | | 5 | | | EN 23015 |
| Transition product | ° C. | | −3 | | | |
| Winter product[1] | ° C. | | see driveability limit | | | |
| CFPP[2] | | | | | | |
| Summer product | ° C. | | −2 | | 0 | EN 116 |
| Transition product | ° C. | | −13 | | −10 | |
| Winter product[1] | ° C. | | see driveability limit | | −20 | |
| Ash content | Weight % | | 0.01 | | 0.01 | EN ISO 6245 |
| Water content | mg/kg | | 200 | | 200 | EN ISO 12937 |
| Oiliness (HFRR WS 1.4) | μm | | 460 | | 460 | ISO 12156-1 |
| Polyaromatic compounds | Weight % | | 11.0 | | 11.0 | IP 391/95 |
| Filtering capacity | min | | 2 | | | SEDAB Test |
| Delivery times | | | | | | |
| Summer product | | 04/15-09/14 | | | 04/15-09/30 | |
| Transition product (autumn) | | 09/15-10/31 | | | 10/01-11/15 | |
| Winter product[1] | | 11/01-02/28 | | | 11/16-02/28 | |
| Transition product (spring) | | 03/01-04/14 | | | 03/01-04/14 | |
| Driveability limit[3] | | | | | | |
| Cloud point | ° C. | −5 | −6 | −7 | −8 | −9 DIN EN 23015 |
| CFPP | ° C. | −30 | −28 | −25 | −23 | −22 DIN EN 116 |

Remarks:
Sampling done according to DIN 51750 T1 + T2
[1] premium diesel (11/01-02/28) with at least 150 mg/L WASA/L diesel
[2] to a maximum of 500 mg MDFI/kg diesel
[3] defined through the combination of cloud point after short sedimentation test and CFPP Especially important in all of this is ignitability, which is described with the cetane number or CN. Briefly explained, one can say that the ignitability of a diesel fuel has an important impact on the engine's combustion process, as well as on noise and emissions. In principle, the higher the cetane number, the shorter the time elapsed between fuel injection and start of combustion (ignition delay). Consequently, the combustion noise decreases as the pressure increase speed decreases. Maximum pressures and temperatures also become lower, something that has a positive effect on nitrogen oxide emissions. In a cold start, a higher cetane number has a favorable impact on HC emissions.

The cetane index given in the standard is alternatively calculated from density and boiling range and is only partially correlated with the CN numbers obtained from the engine because the behavior of ignition accelerators is not taken into account. The CN numbers are determined empirically in special test engines. The compression ratio in the CFR engine and the air intake in the BASF engine can be varied, so that the fuel being tested can be changed.

The objective is to compare the ignitability of the fuel being tested with fuels with known cetane numbers and, if need be, to determine the cetane number through interpolation. In the standard, cetane (n-hexadecane) was arbitrarily assigned the cetane number of 100 and alpha-methyl naphthalene was assigned the cetane number of 0. By mixing the components, one can produce a fuel that will have the same ignitability as the fuel to be tested. The cetane number sought will then correspond to the volumetric share of cetane in the fuel mixture.

To determine the ignitability of a fuel, the test engines are operated in accordance with Table 2.

sensor measuring the cylinder pressure determines the start of combustion. In this case, it is assumed that the start of combustion can be exactly determined with this sensor and the analog processing of the signal. Tests have shown, however, that the curve of the cylinder pressure is only of limited use for determining the start of combustion. In this context, FIG. 1 shows the pressure curves of diesel engines with different combustion processes. According to the principle, the DI engine has the highest pressure increase speed and even the start of combustion which is in the 4-2° CA crankshaft angle before UDP range can still be determined relatively precisely from the pressure. In the swirl chamber engine, however, the determination of the start of combustion becomes significantly harder because of the already slower energy turnover. This problem also applies especially to the test engine when used in a standardized way, as it is executed as a swirl chamber engine too.

Compared to different test engines, the standard gives the accuracy of the process in the 2.8-4.8 CN range. The repeat accuracy lies between 0.8 and 1 CN. Operation is manual and lasts 20-30 minutes per cetane number.

Tests were (and still are being) performed to determine the cetane number with another instrument (especially with vegetable oils) outside of the engine. Thus, the Ignition Quality Tester (IQT) of the Advanced Engine Technology Co. of Ottawa, Ontario, and the Fuel Ignition tester of the Fueltech AS Co, of Trondheim, Norway, are used mostly in Canada and the USA. Both measuring instruments determine the ignitability along the measured ignition delay of the fuel in a

TABLE 2

Dimensions and measuring conditions of the BASF test diesel and the CFR test diesel

| Description | | BASF test diesel | CFR test diesel |
| --- | --- | --- | --- |
| Construction | | Technical testing stand of the Badische Anilin- & Soda Fabrik AG | Cooperative Fuel Research Committee of the American Society of Automotive Engineers |
| Manufacturer | | Hermann Ruf, Mannheim | Waukesha Motor Co., Waukesha, Wisconsin, USA |
| Boring | mm | 90 | S 2.6 |
| Stroke | mm | 120 | 114.3 |
| Displacement | $cm^3$ | 850 | 613 |
| Compression | | Fixed 18.5:1 Volumetric control | Adjustable 6-21:1 |
| Mode of operation | | Swirl chamber | Swirl chamber |
| Measuring procedure and measuring conditions | | | |
| Procedure | | Const. ignition delay | Const. ignition delay |
| RPM | rpm | 1000 ± 10 | 900 ± 9 |
| Intake air temp. | ° C. | 20 ± 5 | 66 ± 1 |
| Coolant temp. | ° C. | 100 ± 2 | 100 ± 2 |
| Oil temperature | ° C. | 70 ± 5 | 57 ± 8 |
| Injection start | °CA b. UDP | 20 | 13 |
| Ignition start | °CA b. UDP | 0 | 0 |
| Injected quantity | $cm^3$/min | 8 ± 0.5 | 13 ± 0.2 |
| Ignition delay display | | Electronic ignition delay meter | Ignition delay meter |
| Standard | | DIN 51 773 | ASTM-D 613 62 T |
| Measuring range | CaZ | 30-100 | 30-100 |

[1]Manufacturer: Hermann Ruf Co., 68 Mannheim-Neckarau
[2]Manufacturer: Waukesha Motor Co., Waukesha, Wisconsin, USA In the CFR engine, the injection point has been fixed to 13° crankshaft angle before upper dead point (° CA b. UDP). The compression ratio is varied in such a way that combustion always starts in the UDP, i.e. with a 13° CA ignition delay. A constant volume, heated high-pressure chamber. Automobile manufacturers are skeptical about the standardization of these processes that take place outside the engine. A fundamental improvement of the engine process has not been found.

The following problem areas have been detected in assessing the standard processes for determining the cetane number:

The accuracy of the process can be improved upon.

The process is time-consuming; it cannot be automated and allows no online display.

In the process, the start of combustion (ignition delay) is determined from the cylinder pressure after analog processing and displayed directly. No exact calculation of the start of combustion takes place.

An evaluation of the cetane numbers of vegetable oils with the needed accuracy has so far been impossible.

The injection moment is set mechanically. There is no operational check with a needle stroke display.

The combustion process in the swirl chamber is no longer contemporary.

It is, therefore, the task of the invention to suggest a process that will make a fast and reliable characterization of the ignitability of fuels possible.

SUMMARY

Objects and advantages of the invention are set forth in part in the following description, or may be obvious from the description, or may be learned through practice of the invention.

In accordance with aspects of the invention, the ignition delay is determined based on the combustion curve and/or the heat curve (heat input through combustion). It is especially suggested to calculate the combustion curve and/or heat curve and, therefrom, the actual start of combustion, which must be known precisely for determining ignition delay, with the laws of thermodynamics (see FIG. 2). The combustion curve and/or heat curve can finally be calculated with mathematical methods based on the first law of thermodynamics (see FIG. 2) known to one skilled in the art. For this, an exact metrological record of cylinder pressure as a function of time or test engine crankshaft angle and, generally, the known caloric data of the fuel are needed.

As input data—and apart from the cylinder pressure—the mass in the cylinder (injected fuel mass and mass of the combustion air supplied) must be metrologically recorded. The final output is at the end the combustion curve and/or heat curve corresponding to the heat input through combustion, although both magnitudes are different from one another merely by the different way in which the wall heat losses of the test engine were considered. The combustion curve and/or heat curve calculated in such a way—it can also be shown that as the change in the fuel mass within the cylinder (dmB) is a function of the crank angle (see FIG. 3)—is significantly steeper than the curve of the pressure at the start of combustion and, therefore, more suitable for determining ignition delay.

DESCRIPTION

Figure 1:
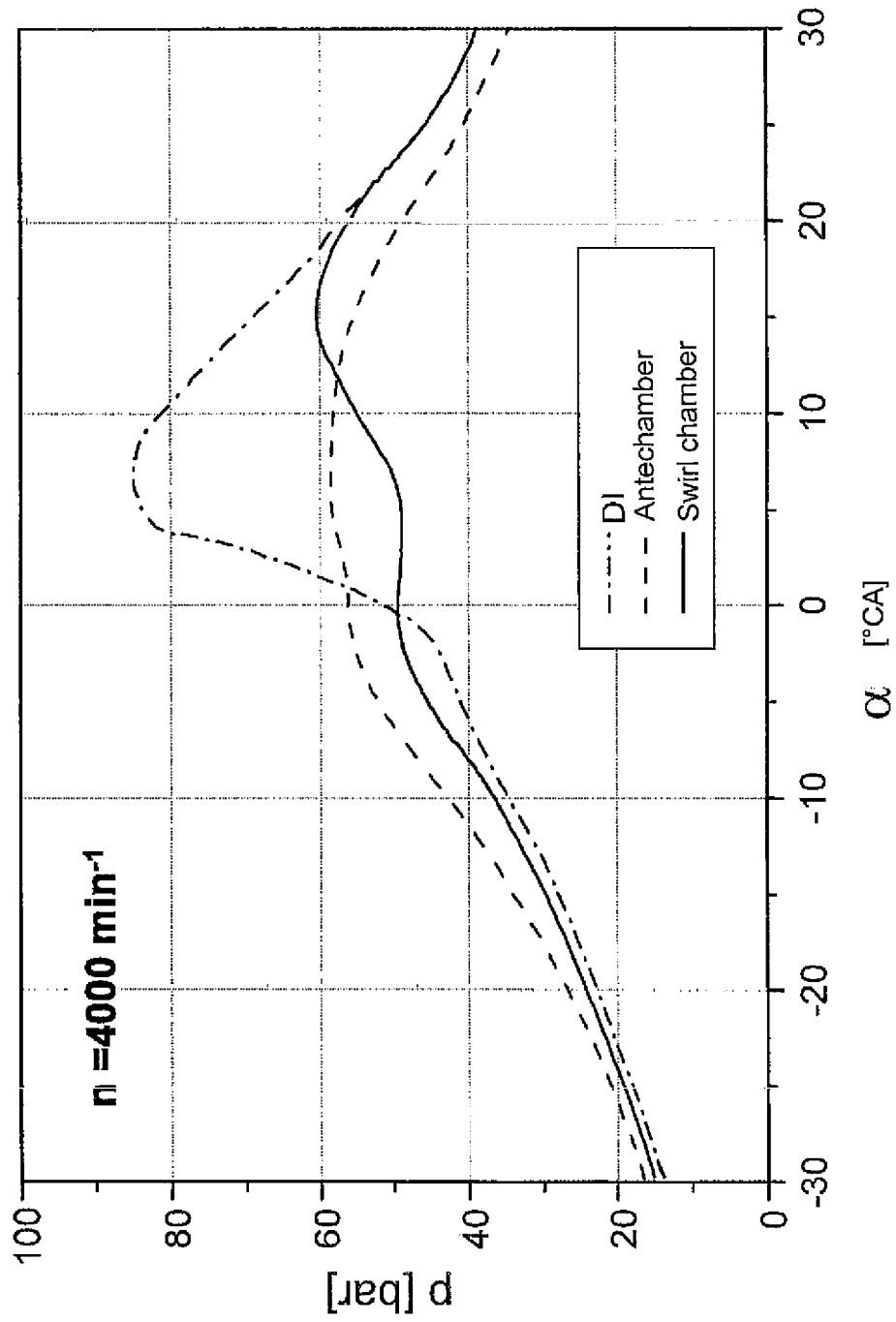
FIG. 1 shows the pressure curves of various diesel engines according to the invention.
Figure 2:
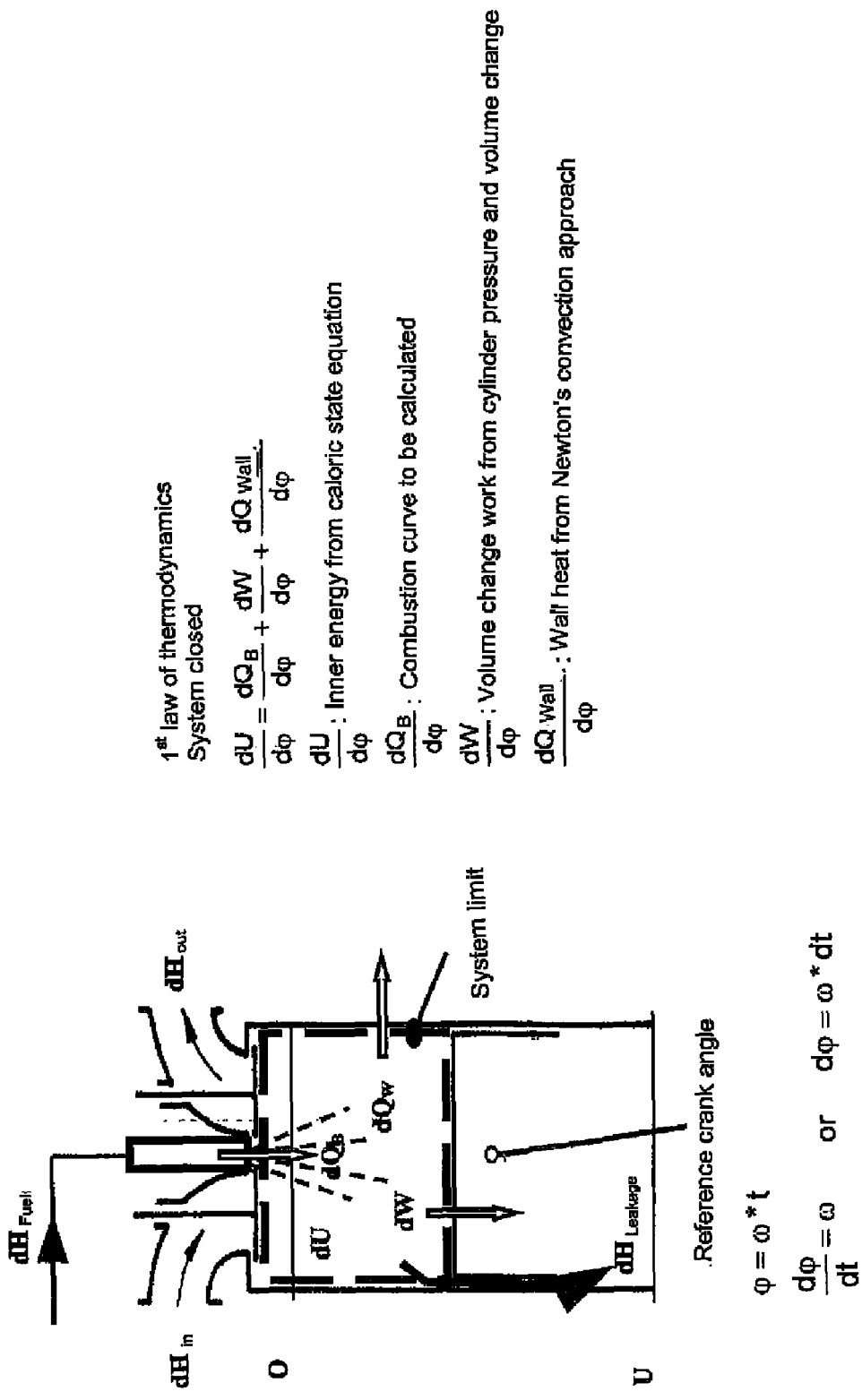
FIG. 2 shows the laws of thermodynamics used to calculate the combustion curve according to the invention.
Figure 3:
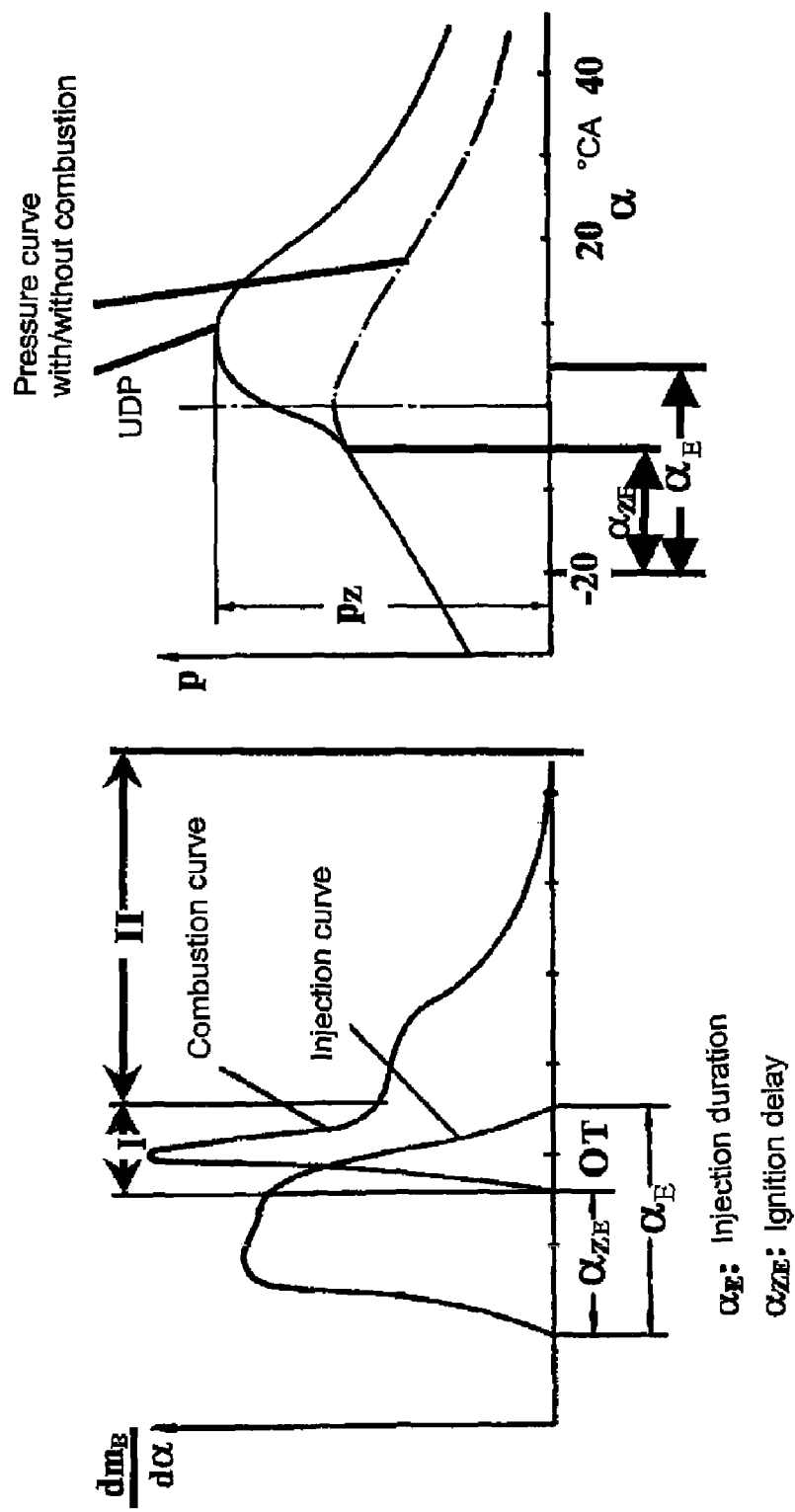
FIG. 3 shows a graph of crankshaft angle versus fuel mass in the cylinder according to the invention.

Reference is now made to particular embodiments of the invention, one or more examples of which are illustrated in the drawings. Each embodiment is provided by way of explanation of the invention, and not as a limitation of the invention. For example, features illustrated as described as part of one embodiment may be used with another embodiment to yield still a further embodiment. It is intended that the present invention include these and other modifications and variations.

To improve the accuracy of the process, it is necessary to determine the start of injection apart from the start of combustion. To determine the start of injection, it is recommended to equip the injector with a needle stroke sensor so the lifting of the injector needle is recognized and the actual start of injection can be measured exactly and independently from other parameters. If the injector is electromagnetically or piezoelectrically controlled, it is also possible, as an alternative, to determine the needle stroke from the control signal (voltage measurement and consideration of additional injector performance characteristics, if applicable), instead of using the needle stroke sensor.

Figure 4:
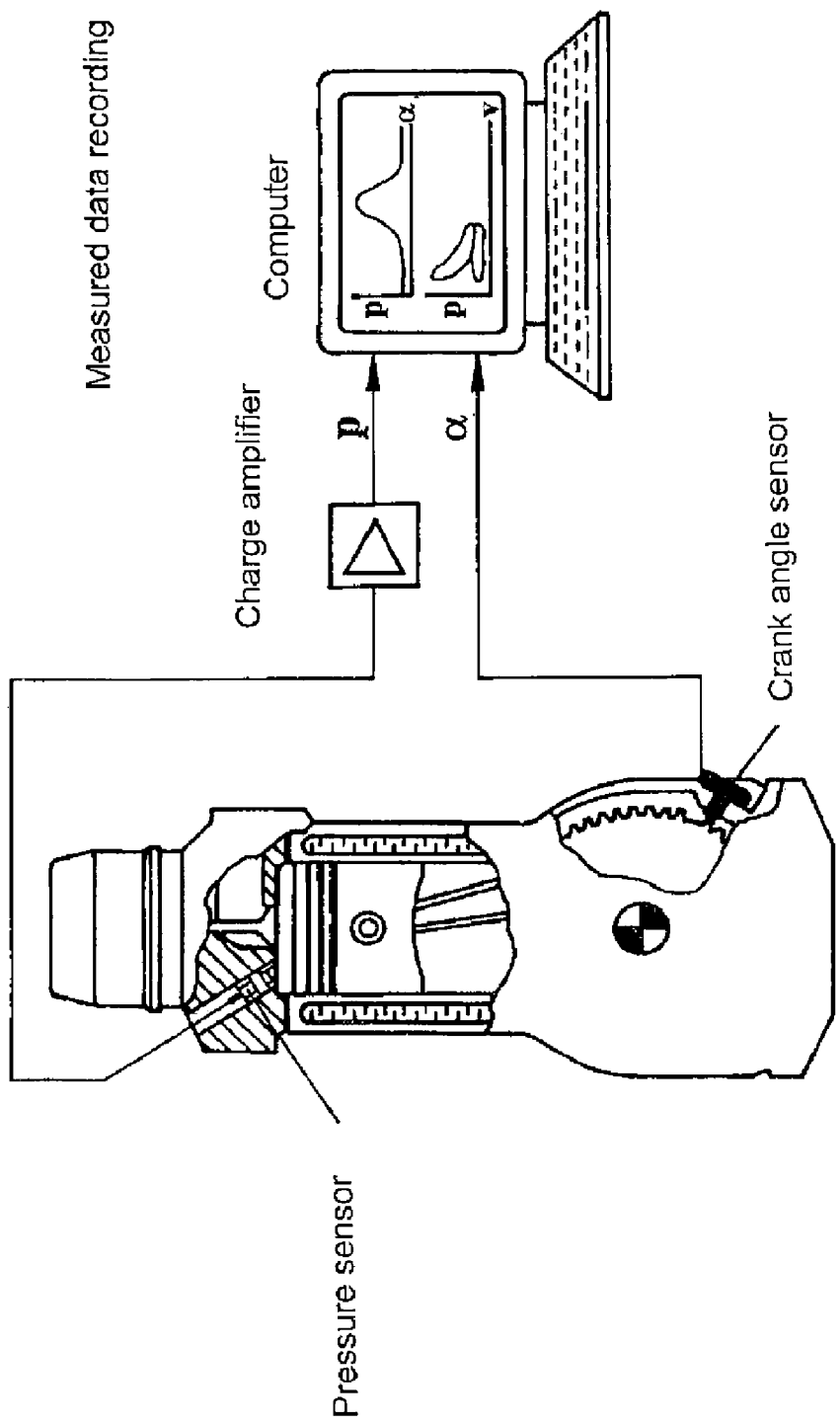
FIG. 4 shows a pressure sensor system according to the invention.

A built-in piezoelectric pressure sensor (like the one typically employed in the R&D tasks of engine developers) is used for measuring cylinder pressure. The signal is amplified and converted to a voltage signal proportional to the cylinder pressure (FIG. 4). The voltage signal is fed to a fast measurement data recording system, where it is digitalized, further processed, and stored. In this case, the recording of the pressure data is done based on time and/or crankshaft angle. A corresponding sensor is intended for placement on the crank shaft (FIG. 4). The air mass sucked in must be determined with an air mass meter. The injected quantity (=fuel mass) is fixed and can be determined in preliminary tests done on a pump testing stand. The combustion process should be advantageously adapted for direct injection.

Examples of the process steps are listed below:

Crankshaft angle-based measurement of the cylinder pressure signal (scanning frequency: 0.2° CA)

Measurement of the air mass sucked in.

Measurement of the needle stroke (scanning frequency: 0.2° CA) for determining the start of injection.

Calculation of the determined needle stroke and pressure valve from 300 working examples.

Calculation of the combustion curve and/or heat curve.

Calculation of the ignition delay from the combustion curve and/or heat curve and the corresponding start of injection.

Correlation of results with the known standard fuels or their mixtures or also with previously analyzed fuels of known composition and/or ignitability.

Calculation, display, and storage of the cetane number determined.

The important advantages of the device and process include:

Higher accuracy, especially in calculating the combustion curve and heat curve, respectively Higher accuracy because the needle stroke is measured.

Higher repeat accuracy by obtaining the average from approx. 300 working examples Possibility of automation.

Online display of the cetane number.

Automatic or partially-automatic execution.

Measurement with regular gasoline no longer needed, as the results can be made available in a database. The compression ratio can be exactly calculated from the pressure curve before the moment of ignition.

Current DI combustion process.

Can be used with vegetable oils.

Modifications of the invention are easily possible within the framework of the patent claims, in which case, it is expressly mentioned that all individual characteristics set forth in the patent claims, in the description, and in the figures can become reality in any combination thereof, as far as it is possible and makes sense. Thus, for example, a previously defined value for the combustion curve and/or heat curve, such as the start of combustion can be determined with the help of a sensor, especially one for measuring an ionic current inside the test engine, a sensor for measuring the structure-borne noise of the test engine and/or an optical sensor. It can, likewise, be advantageous for the determination of ignitability to include a statistical analysis of one or several of the measured values mentioned so far. In this case, it is once again advantageous if the statistical analysis includes the recording of measured values of several successive working cycles. The statistical analysis can also encompass the recording of one or several measured values (for example, of 200 to 300 working cycles) of the test engine, especially in a defined operational point of the test engine. In this way, many different readings are obtained from which averages can be calculated, so that the ignition delay can be determined with a great deal of accuracy.

Modifications and variations can be made to the embodiments illustrated or described herein without departing from the scope and spirit of the invention as set forth in the appended claims.

The invention claimed is:

1. A method for determining ignitability of a fuel, particularly ignitability of a self-igniting fuel, in a test engine, the method comprising:
   calculating a combustion curve or heat curve for the test engine;
   determining actual start of fuel injection by detecting actual lifting of an injector needle in the test engine;
   calculating ignition delay of the fuel from the combustion curve or heat curve and the determined actual start of fuel injection; and
   comparing the calculated ignition delay of the fuel with the ignition delay of at least one comparative fuel with a known ignitability to determine the ignitability of the tested fuel.

2. The method according to claim 1, wherein at least one of start of combustion, duration of combustion, the central combustion zone, or maximum combustion speed are determined from the combustion curve or heat curve, and wherein the combustion curve or heat curve is determined via a sensor for measuring any one or combination of ionic current inside the test engine, structure-borne noise of the test engine, or an optical sensor.

3. The method according to the claim 1, wherein cetane (CN 100), alpha-methyl naphthalene (CN 20), or heptamethylnonane (CN 15) are used as the comparative fuel.

4. The method according to claim 1, wherein a characteristic number that describes the ignitability of the fuel is determined based on a state variable consisting of any combination of pressure, temperature, a volume of gases being produced during combustion, or dwelling time of the fuel.

5. The method according to claim 1, further comprising converting the ignitability of the fuel to a corresponding cetane number.

6. The method according to claim 1, wherein a one or more parameters of start of combustion, the duration of combustion, central combustion zone, or maximum combustion speed are determined from the combustion curve or heat curve and, based on at least one of these parameters and into the test engine, the ignition delay is determined therefrom.

7. The method according to claim 1, wherein a cylinder pressure is detected during the combustion of the fuel in the test engine and used for determining the combustion curve or the heat curve.

8. The method according to claim 7, wherein the cylinder pressure is measured as a function of time or crankshaft angle of the test engine cylinder.

9. The method according to claim 8, wherein the crankshaft angle of the test engine is determined via a crank angle sensor, especially as a function of time.

10. The method according to claim 7, wherein the cylinder pressure is detected via a piezoelectric cylinder pressure sensor.

11. The method according to claim 1, wherein the start of fuel injection is metrologically recorded.

12. The method according to claim 1, wherein the start of fuel injection is recorded via a needle stroke sensor.

13. The method according to claim 1, wherein the ignition delay is calculated from a difference of the start of fuel injection and the start of combustion or an additional characteristic point of combustion.

14. The method according to claim 1, wherein the combustion curve or the heat curve is calculated as a function of the test engine crankshaft angle.

15. The method according to claim 1, wherein the combustion curve or the heat curve is calculated from measured data from a single working cycle of test engine.

16. The method according claim 1, wherein the combustion curve or the heat curve is calculated based on measured data from several test engine working cycles, wherein corresponding averages of the measured data are calculated from the several working cycles.

17. The method according to claim 1, wherein the fuel is injected into the test engine cylinder by direct injection or using a side chamber process.

18. The method according to claim 1, wherein any one or combination of volume flow of combustion air flowing into the test engine, mass of combustion air flowing into the test engine, change of volume or mass of combustion air flowing into the test engine as a function of time, or crankshaft angle is used for determining the combustion curve or the heat curve.

19. The method according to claim 1, wherein pressure increase speed is taken into account during combustion of the fuel in the test engine when determining the ignitability.

20. The method according to claim 1, wherein the determination of the ignitability includes a statistical analysis of the measured data.

21. The method according to claim 20, wherein the statistical analysis encompasses recording the measured data of several successive working cycles.

22. The method according to claim 20, wherein the statistical analysis encompasses the recording of measured data from one or several working cycles, particularly in a defined operational point of the test engine.

23. The method according to claim 20, wherein the statistical analysis includes the calculation of averages of the measured parameters.

24. The method according to claim 1, wherein a test engine compression ratio is calculated based on cylinder pressure at a defined crankshaft angle.

25. The method according to claim 1, wherein the calculations and the control of individual process steps take place automatically via a control unit.

26. The method according to claim 1, wherein the values of the measured parameters or the determined ignitability are displayed online.

* * * * *